United States Patent
Gilbert

(10) Patent No.: US 8,377,054 B2
(45) Date of Patent: Feb. 19, 2013

(54) AUTOMATIC CONTROL CIRCUIT FOR USE IN AN ELECTROSURGICAL GENERATOR

(75) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 574 days.

(21) Appl. No.: 12/566,173

(22) Filed: Sep. 24, 2009

(65) Prior Publication Data

US 2011/0071521 A1   Mar. 24, 2011

(51) Int. Cl.
*A61B 18/10* (2006.01)
(52) U.S. Cl. .......................................... 606/34; 606/41
(58) Field of Classification Search ............. 606/32–35, 606/41, 42, 48–50
See application file for complete search history.

(56) References Cited

U.S. PATENT DOCUMENTS

| | | | |
|---|---|---|---|
| 5,372,596 A * | 12/1994 | Klicek et al. ..................... 606/35 |
| 5,722,975 A | 3/1998 | Edwards |
| 5,776,130 A | 7/1998 | Buysse et al. |
| 7,215,986 B2 * | 5/2007 | Diab et al. ..................... 600/336 |
| 7,300,435 B2 * | 11/2007 | Wham et al. ..................... 606/34 |
| 7,956,620 B2 | 6/2011 | Gilbert |
| 8,152,802 B2 | 4/2012 | Podhajsky et al. |
| 8,162,932 B2 | 4/2012 | Podhajsky et al. |
| 8,167,875 B2 | 5/2012 | Podhajsky et al. |
| 8,174,267 B2 | 5/2012 | Brannan et al. |
| 8,180,433 B2 | 5/2012 | Brannan et al. |
| 8,211,100 B2 | 7/2012 | Podhajsky et al. |
| 8,226,639 B2 | 7/2012 | Podhajsky et al. |
| 8,231,553 B2 | 7/2012 | Joseph et al. |
| 8,235,917 B2 | 8/2012 | Joseph et al. |
| 8,242,782 B2 | 8/2012 | Brannan et al. |
| 2005/0070896 A1 | 3/2005 | Daniel et al. |
| 2005/0101949 A1 | 5/2005 | Harano et al. |
| 2005/0113819 A1 * | 5/2005 | Wham et al. ..................... 606/34 |
| 2005/0203504 A1 * | 9/2005 | Wham et al. ..................... 606/34 |
| 2009/0254077 A1 | 10/2009 | Craig |
| 2009/0292283 A1 | 11/2009 | Odom |
| 2010/0030210 A1 * | 2/2010 | Paulus ............................ 606/38 |
| 2010/0057076 A1 | 3/2010 | Behnke et al. |
| 2010/0063494 A1 | 3/2010 | Orszulak |
| 2010/0063497 A1 | 3/2010 | Orszulak |
| 2010/0079215 A1 | 4/2010 | Brannan et al. |
| 2010/0082022 A1 | 4/2010 | Haley et al. |
| 2010/0082083 A1 | 4/2010 | Brannan et al. |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

James Gilbert, Polyphase Demodulation and Filter versus the Goertxzel DFT, A.V. Oppenheim and R. W. Schafer, Discrete-Time Signal Prcoessing, Prentice-Hall, 1990.

(Continued)

*Primary Examiner* — Michael Peffley

(57) ABSTRACT

An automatic control circuit for an electrosurgical generator is herein disclosed. The automatic control circuit includes voltage and current sensing circuits, a processing circuit, a dosage calculating circuit, and control circuit. Samples of the voltage and current outputs are supplied to the processing circuit and the dosage calculating circuit to generate a dosage output signal. The dosage output signal is compared to a reference signal to generate a feedback signal that controls a drive circuit.

13 Claims, 4 Drawing Sheets

U.S. PATENT DOCUMENTS

| | | |
|---|---|---|
| 2010/0082084 A1 | 4/2010 | Brannan et al. |
| 2010/0094271 A1 | 4/2010 | Ward et al. |
| 2010/0094288 A1 | 4/2010 | Kerr |
| 2010/0179533 A1 | 7/2010 | Podhajsky |
| 2010/0179538 A1 | 7/2010 | Podhajsky |
| 2011/0028963 A1 | 2/2011 | Gilbert |
| 2011/0054460 A1 | 3/2011 | Gilbert |
| 2011/0060329 A1 | 3/2011 | Gilbert et al. |
| 2011/0071516 A1 | 3/2011 | Gregg |
| 2011/0071521 A1 | 3/2011 | Gilbert |
| 2011/0077631 A1 | 3/2011 | Keller |
| 2011/0112530 A1 | 5/2011 | Keller |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 0640317 A1 | 3/1995 |
| EP | 836868 | 4/1998 |
| EP | 1051948 | 11/2000 |
| EP | 1263181 | 12/2002 |
| EP | 1472984 A1 | 11/2004 |
| EP | 1500378 A1 | 1/2005 |
| EP | 880220 | 6/2006 |
| EP | 2025297 | 2/2009 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| SU | 166452 | 1/1965 |
| SU | 727201 | 4/1980 |
| WO | WO 94/10922 A1 | 5/1994 |
| WO | WO 94/24949 A1 | 11/1994 |
| WO | WO02/11634 | 2/2002 |
| WO | WO02/45589 | 6/2002 |
| WO | WO03/090635 | 11/2003 |
| WO | WO2006/050888 | 5/2006 |

OTHER PUBLICATIONS

Wald et al., "Accidental Burns", JAMA, Aug. 16, 1971, vol. 217, No. 7, pp. 916-921.

Vallfors et al., "Automatically Controlled Bipolar Electrosoagulation-'COA-COMP'" Neurosurgical Review 7:2-3 (1984) pp. 187-190.

Sugita et al., "Bipolar Coagulator with Automatic Thermocontrol" J. Neurosurg., vol. 41, Dec. 1944, pp. 777-779.

Muller et al. "Extended Left Hemicolectomy Using the LigaSure Vessel Sealing System" Innovations That Work; Company Newsletter; Sep. 1999.

Ogden Goertzel Alternative to the Fourier Transform: Jun. 1993 pp. 485-487 Electronics World; Reed Business Publishing, Sutton, Surrey, BG vol. 99, No. 9. 1687.

Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

Richard Wolf Medical Instruments Corp. Brochure, "Kleppinger Bipolar Forceps & Bipolar Generator" 3 pp. Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Geddes et al., "The Measurement of Physiologic Events by Electrical Impedence" Am. J. MI, Jan. Mar. 1964, pp. 16-27.

Cosman et al., "Methods of Making Nervous System Lesions" In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Cosman et al., "Radiofrequency Lesion Generation and Its Effect on Tissue Impedance" Applied Neurophysiology 51: (1988) pp. 230-242.

Ni W. et al. "A Signal Processing Method for the Coriolis Mass Flowmeter Based on a Normalized . . ." Journal of Applied Sciences-Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297 Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone" Neurosurgery 15:(1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300" 1 p. Sep. 1998.

Valleylab Brochure "Valleylab Electroshield Monitoring System" 2 pp. Nov. 1995.

International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.

International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09164754.5 dated Aug. 21, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US09/46870 dated Jul. 21, 2009.
Extended European Search Report from European Patent Application No. 07001494.9 mailed Mar. 7, 2011.
International Search Report EP10179363 dated Jan. 12, 2011.
Fredric J. Harris et al., Digital Receivers and Transmitters Using Polyphase Filter Banks for Wireless Communications, Apr. 2003, pp. 1395-1412, vol. 51, No. 4, IEEE Transactions on Microwave Theory and Techniques.
U.S. Appl. No. 10/406,690, filed Apr. 3, 2003, Klicek.
U.S. Appl. No. 10/573,713, filed Mar. 28, 2006, Wham.
U.S. Appl. No. 11/242,458, filed Oct. 3, 2005, Becker.

* cited by examiner

AUTOMATIC CONTROL CIRCUIT FOR USE IN AN ELECTROSURGICAL GENERATOR

BACKGROUND

1. Technical Field

The present disclosure relates to electrosurgery. More particularly, the present disclosure relates to an automatic control circuit for an electrosurgical generator.

2. Background of Related Art

Surgeons typically try to regulate energy application by adjusting the basic power level of the electrosurgical generator and using the hand or foot switch to control the power applied over time. Unfortunately, that technique may lead to unintended power delivery or undesired duration of power delivery to the surgical site. Surgeons may also experience difficulty in repeatably and/or consistently desiccating tissue to the desired levels due to the limits of their human reaction time or machine response time when manual or foot activated switches are used for manual control. In addition, during endoscopic procedures, surgeons lose some visual and tactile indications of desiccation progression.

Calculations of feedback signals that are useful in the control of radio frequency (RF) electrosurgical instruments during operation can be summarized in two general forms. Analog computations tend to use expensive high frequency analog Root Mean Square (RMS) to direct current (DC) algorithms or circuits or less expensive Mean Absolute Deviation (MAD) circuits for computing the true, or near true in the case of MAD, RMS values of voltage and current which can be used to calculate power or impedance using Ohm's law. Additional methods are employed to calculate the load voltage to current phase angle in order to compensate for the reactive loading or the power factor (PF). Analog circuits typically have exponential responses or further filtering on PF and/or power which may result from a compromise between accuracy and response time. Calibration may also be difficult to maintain due to manufacturing and temperature variations.

Digital computations often mimic the analog implementation by computing the RMS values directly from digitized waveforms for voltage and current and then applying the phase angle or PF corrections. A circuit for automatically controlling the output of an electrosurgical generator utilizing digital computations is disclosed in U.S. Pat. No. 7,300,435 to Wham et al., assigned to Sherwood Services AG, the contents of which are hereby incorporated by reference in their entirety. U.S. Pat. No. 7,300,435 relates to an automatic control system that uses the phase difference between the voltage and current waveforms as calculated using a Goertzel algorithm to adjust the current, voltage or power delivered to the patient.

SUMMARY

An automatic control system for an electrosurgical generator is disclosed. Automatic control system includes voltage and current sensing circuits, a processing circuit, a dosage calculating circuit, and a comparison circuit. The voltage and current sensing circuits produce voltage and current signals that are representative of the voltage and current present in the output of the electrosurgical generator. These signals are processed using a polyphase demodulation and decimation filter to determine the magnitude and power factor of the voltage and the current waveforms.

The processing circuit produces an output signal that is communicated to the dosage calculating circuit for determining the dosage output of the electrosurgical generator. The dosage calculating circuit produces a dosage output signal that is compared to a reference signal in the comparison circuit. The comparison circuit determines the difference between the dosage output signal and the reference signal and generates a feedback signal that is representative of the difference. The feedback signal is communicated to control the output of a drive control circuit.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1A:
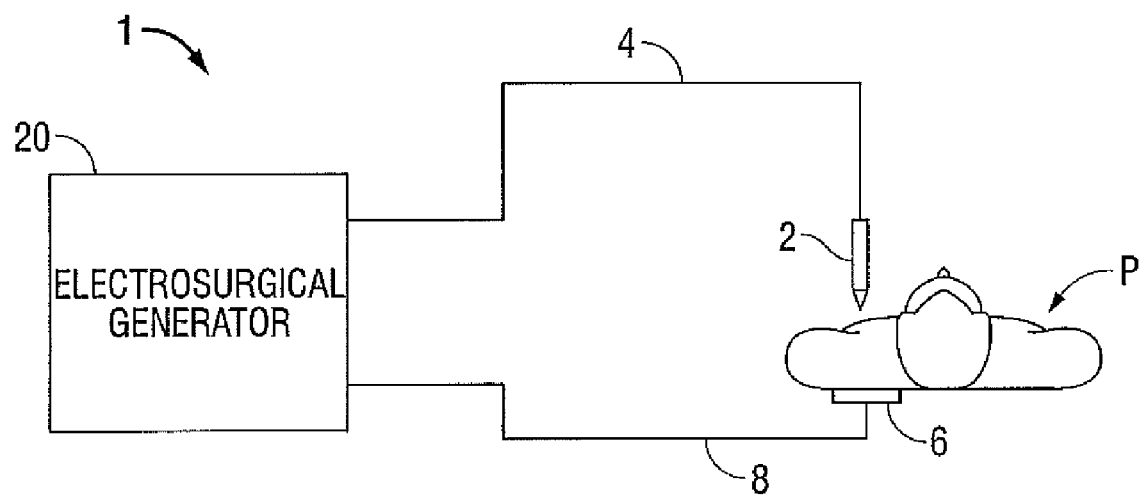
FIGS. 1A-1C are schematic block diagrams of electrosurgical systems in accordance with an embodiment of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The generator according to the present disclosure can perform ablation, monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, ablation needle, etc.). Further, the generator includes electronic circuitry configured for generating radio frequency power specifically suited for various electrosurgical modes (e.g., cutting, blending, division, etc.) and procedures (e.g., ablation, monopolar, bipolar, vessel sealing).

FIG. 1A is a schematic illustration of a monopolar electrosurgical system 1 according to one embodiment of the present disclosure. The system 1 includes an electrosurgical instrument 2 having one or more electrodes for treating tissue of a patient P. The instrument 2 is a monopolar type instrument including one or more active electrodes (e.g., electrosurgical cutting probe, ablation electrode(s), etc.). Electrosurgical RF energy is supplied to the instrument 2 by a generator 20 via a supply line 4, which is connected to an active terminal 120 (FIG. 2) of the generator 20, allowing the instrument 2 to coagulate, ablate and/or otherwise treat tissue. The energy is returned to the generator 20 through a return electrode 6 via a return line 8 at a return terminal 130 (see FIG. 2) of the generator 20. The active terminal 120 and the return terminal 130 are connectors configured to interface with plugs (not explicitly shown) of the instrument 2 and the return electrode 6, which are disposed at the ends of the supply line 4 and the return line 8, respectively.

The system 1 may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage. In one embodiment, the active electrode 6 may be used to operate in a liquid environment, wherein the tissue is submerged in an electrolyte solution.

Figure 1B:
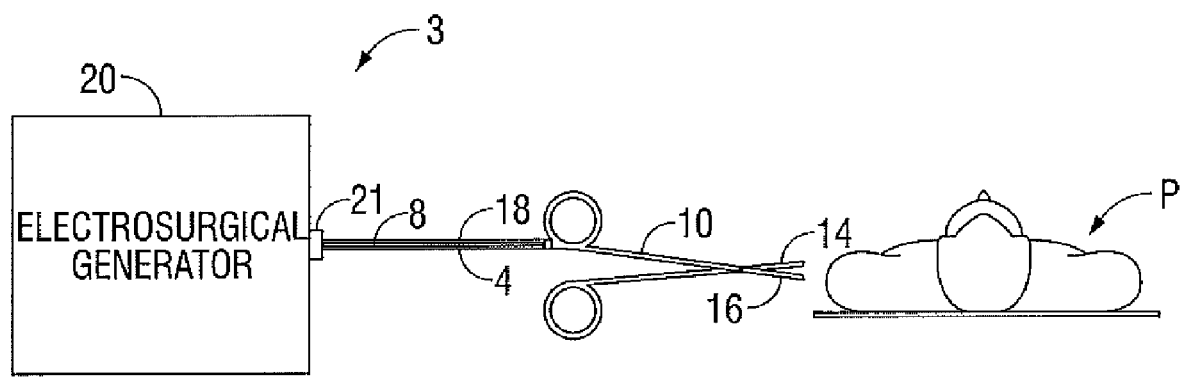

FIG. 1B is a schematic illustration of a bipolar electrosurgical system 3 according to the present disclosure. The system 3 includes a bipolar electrosurgical forceps 10 having one or more electrodes for treating tissue of a patient P. The electrosurgical forceps 10 include opposing jaw members having an active electrode 14 and a return electrode 16, respectively, disposed therein. The active electrode 14 and the return electrode 16 are connected to the generator 20 through cable 18, which includes the supply and return lines 4, 8 coupled to the active and return terminals, 120 and 130, respectively (see FIG. 2). The electrosurgical forceps 10 are coupled to the generator 20 at a connector 21 having connections to the active and return terminals 120 and 130 (e.g., pins) via a plug disposed at the end of the cable 18, wherein the plug includes contacts from the supply and return lines 4, 8.

Figure 1C:
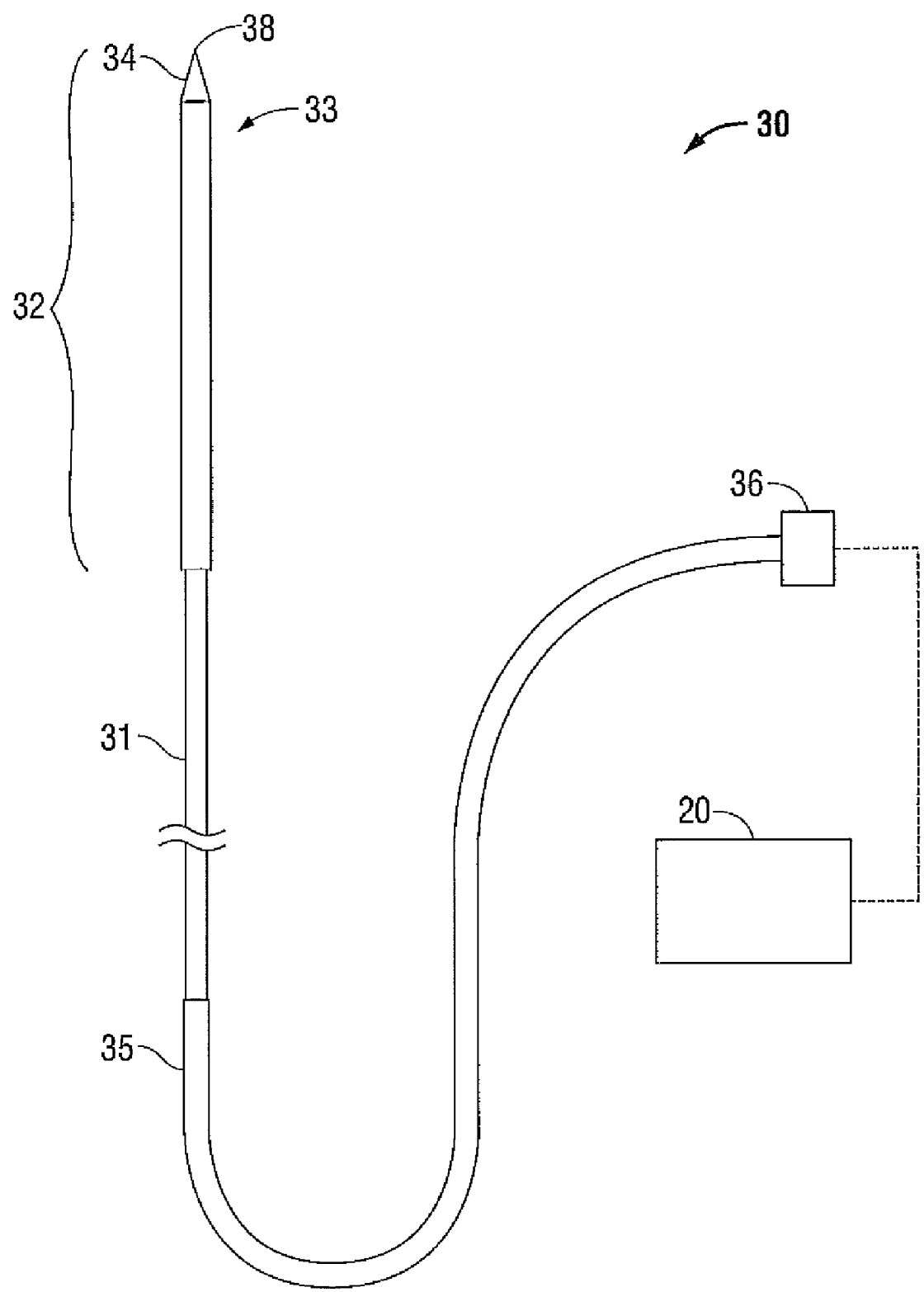

FIG. 1C is a schematic illustration of a microwave antenna assembly 30 in accordance with one embodiment of the present disclosure. Antenna assembly 100 includes a radiating portion 32 that is connected by feedline 31 (or shaft) via cable 35 to connector 36, which may further connect the assembly 30 to a generator 20, e.g., a microwave and/or RF electrosurgical generator. Assembly 30, as shown, is a dipole microwave antenna assembly, but other antenna assemblies, e.g., monopole or leaky wave antenna assemblies, may also utilize the principles set forth herein. Distal radiating portion 33 of radiating portion 32 includes a tapered end 34 which terminates at a tip 38 to allow for insertion into tissue with minimal resistance. It is to be understood, however, that tapered end 34 may include other shapes, such as without limitation, a tip 38 that is rounded, flat, square, hexagonal, or cylindroconical.

The generator 20 may include a plurality of connectors to accommodate various types of electrosurgical instruments (e.g., instrument 2, electrosurgical forceps 10, etc.). Further, the generator 20 may operate in monopolar or bipolar modes by including a switching mechanism (e.g., relays) to switch the supply of RF energy between the connectors, such that, for instance, when the instrument 2 is connected to the generator 20, only the monopolar plug receives RF energy.

Figure 2:
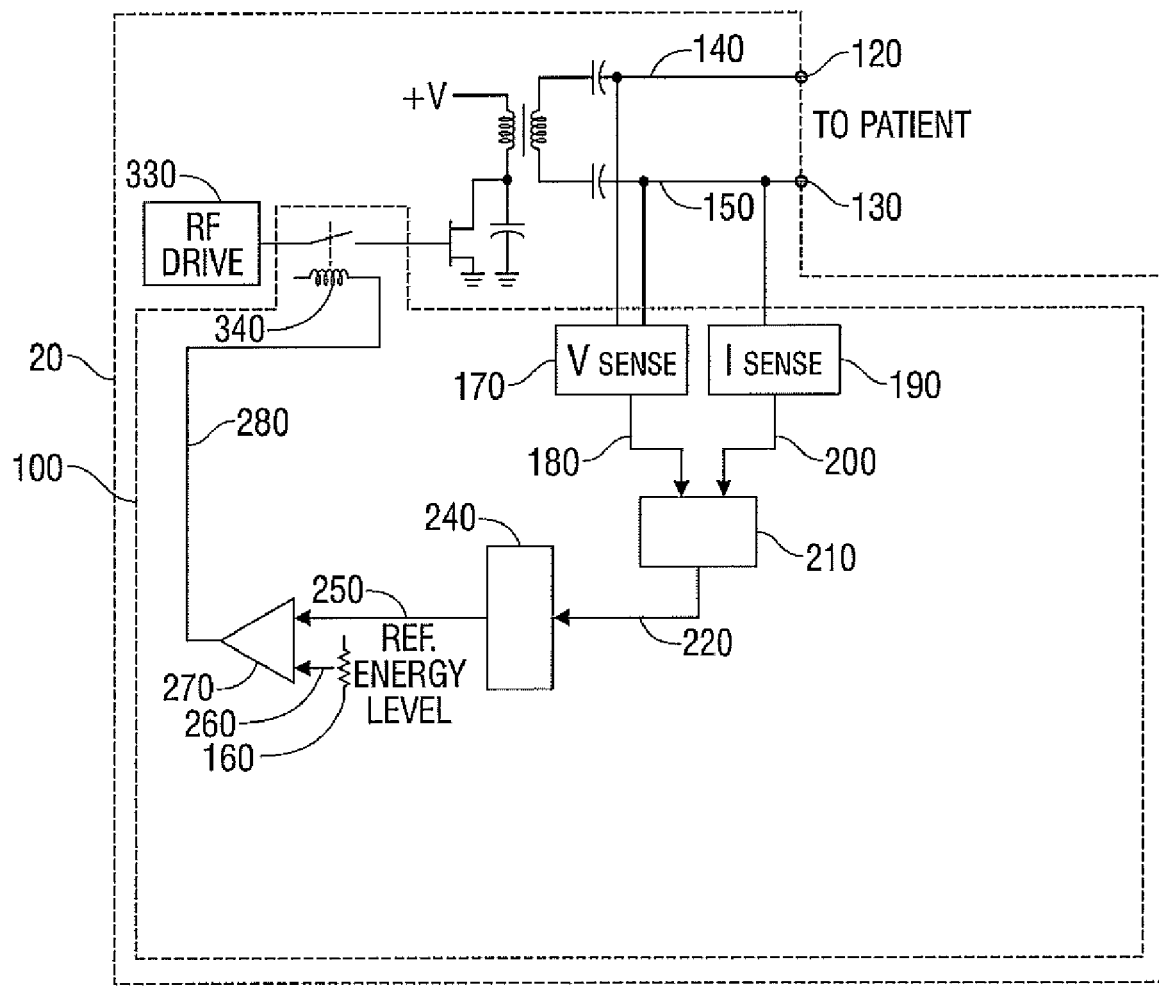
FIG. 2 is block diagram of an automatic control circuit in an electrosurgical generator in accordance with an embodiment of the present disclosure.

Referring to FIG. 2, an embodiment of the presently disclosed automatic control circuit 100 is illustrated. Automatic control circuit 100 is preferably disposed within an electrosurgical generator 20 but may be disposed within the instrument (e.g., instrument 2, electrosurgical forceps 10, etc.). Electrosurgical generator 20 includes a user control 160 preferably on a front panel thereof that is accessible to the doctor for setting the level of energy desired for electrosurgery. User control 160 may be in the form of a knob, slider, or the like for use by the clinician to set a reference signal 260 indicative of the energy level desired.

A voltage sensing circuit 170, has an isolation transformer or other similar high voltage sensing means that acts as an inductive pickup with a primary winding connected between leads 140 and 150 that induces the secondary windings to provide a voltage signal 180 and thus, responds to high frequency electrosurgical energy supplied by electrosurgical generator 20 and flowing through leads 140 and 150. A current sensing circuit 190 responds to high frequency electrosurgical energy supplied by electrosurgical generator 20 and flowing through return lead 150. Current sensing circuit 190 is capable of providing a current signal 200 instantaneously passing therethrough. Voltage signal 180 and current signal 200 may be AC waveforms that are representative of the output of leads 140 and 150.

Leads 140 and 150 operatively connected to electrodes 120 and 130. Electrodes 120 and 130 are used to provide the output of electrosurgical generator 20 to a patient. In a bipolar configuration, electrodes 120 and 130 are both present in an electrosurgical instrument that is used at a surgical site of the patient with electrode 130 providing the return path for the output of electrosurgical generator 20.

In a monopolar configuration, the electrosurgical instrument (not shown) includes one electrode 120 while electrode 130 is connected to a surface near the patient and provides the return path. The active ends of electrodes 120 and 130 are electrically connected to electrosurgical generator 20 by one or more conductive cables. Although monopolar and bipolar configurations are used in electrosurgical generators, they are electrically equivalent and equally suited for use with automatic control circuit 100 of the present disclosure.

Voltage sensing circuit 170 and current sensing circuit 190 are operatively coupled to a processing circuit 210. In a particular embodiment, processing circuit 210 includes one or more digital signal processors (DSP) or devices capable of performing DSP functions and associated circuitry. The DSPs are upgradeable using flash ROM as is known in the art. Upgrades for the DSPs may be stored on computer readable media such as magnetic disks, optical disks, magnetic tape, or other media as is known in the art. Processing circuit 210 simultaneously receives voltage signal 180 and current signal 200.

Figure 3:
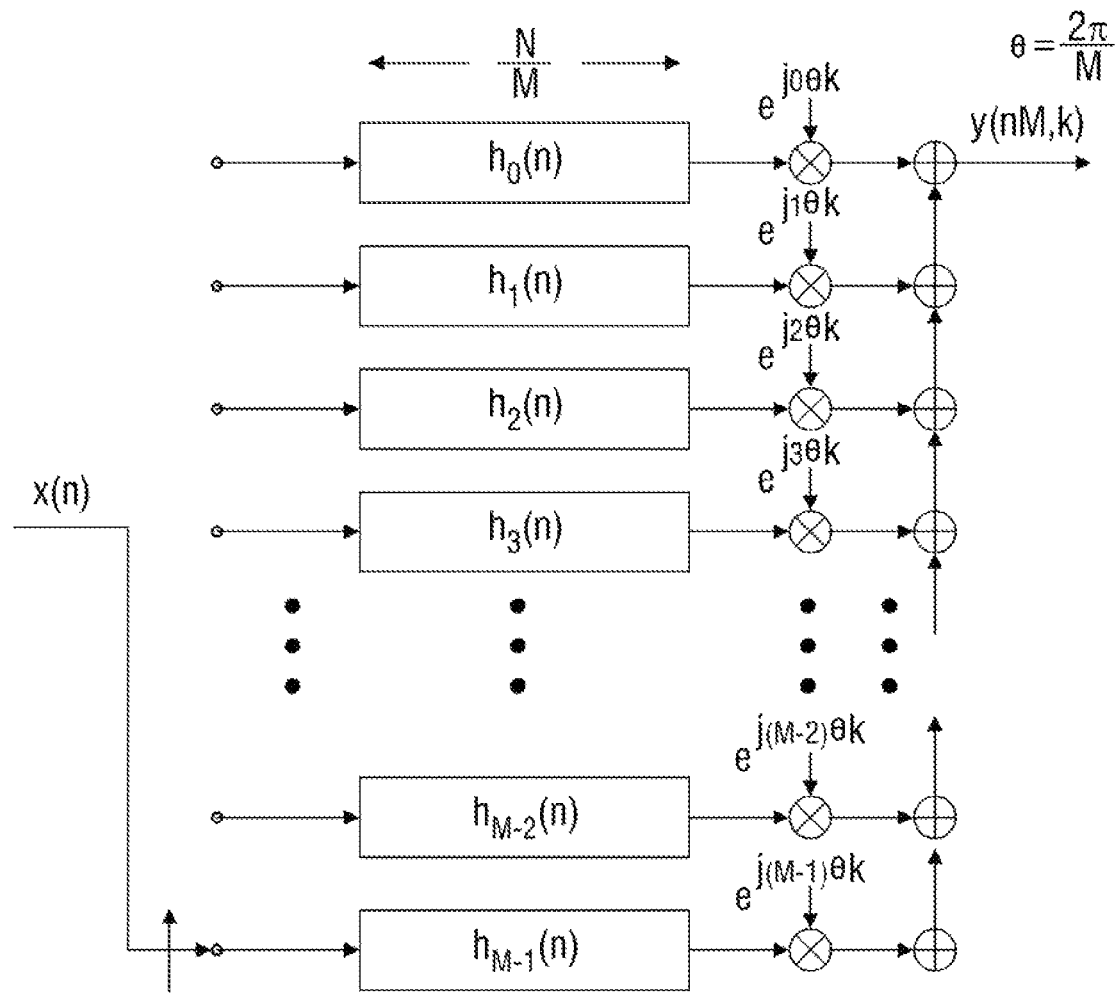
FIG. 3 is a block diagram of a polyphase structure in accordance with an embodiment of the present disclosure.

Processing circuit 210 implements a polyphase demodulation and decimation filter to calculate a feedback signal. A polyphase demodulation and decimation filter structure having a length N/M is shown in FIG. 3. As shown in FIG. 3, an appropriately designed decimation filter h(n) of length L-points and total decimation rate at the output of M is applied to the input x(n). In a polyphase decimation filter, the output sample rate is 1/M times the input sample rate, with M being the decimation factor. Polyphase filters can simplify the overall design and reduce the number of computations needed. Each filter output is multiplied by a complex heterodyne of the form $e^{jn\theta k}$ where θ equals 2π/M and constant k is the ratio of the modulating frequency θ to the decimation frequency or the integer number of periods of the modulating frequency at the output sample rate. The modulating frequency θ is chosen in order to modulate the signal to a baseband frequency that is usually 0 or DC. The products of the filter outputs and the heterodyne function are added together and outputted as a complex function y(nM,k). The output of the polyphase demodulated and decimation filter can be given by the following difference equation:

$$S_k(n \cdot M) = \sum_{r=0}^{M-1} e^{-j \cdot r \cdot \frac{2\pi \cdot k}{M}} \cdot \sum_{m=0}^{\frac{N}{M}-1} [x[(n-m) \cdot M - r] \cdot h(r + m \cdot M)]. \quad (1)$$

The computational advantage of applying such a polyphase finite impulse response (FIR) structure may not be immediately apparent until it is recognized that an advantage may be gained through a reduction of the overall filter length, N-points to L-points by carefully designing h[n] as an equivalent performing FIR filter to that of a simple "box-car" windowed infinite impulse response (IIR). The expected improvement is a reduction in the number of computations per output point with a filter of a predetermined length.

In one particular embodiment, the DSPs of processing circuit 210 include the polyphase demodulation and decimation filter along with associated processing software to determine the phase difference between voltage signal 180 and current signal 200. Additionally, processing circuit 210 determines the magnitude of both voltage and current signals 180, 200 and communicates these values along with the power factor to a dosage calculating circuit 240 as output signal 220. Voltage signal 180 and current signal 200 have a real portion and an imaginary portion which can be represented by the equations:

$$E = E_{RMS} \cdot e^{j\theta 1} = E_{RMS} \cdot \cos\theta 1 + E_{RMS} \cdot j\sin\theta 1 = \text{Real}\{E_k[n \cdot M]\} + j\text{Imaginary}\{E_k[n \cdot M]\} \quad (2a)$$

$$I = I_{RMS} \cdot e^{j\theta 2} = I_{RMS} \cdot \cos\theta 2 + I_{RMS} \cdot j\sin\theta 2 = \text{Real}\{I_k[n \cdot M]\} + j\text{Imaginary}\{I_k[n \cdot M]\}. \quad (2b)$$

In one embodiment, dosage calculating circuit 240 includes a microprocessor with associated circuitry for calculating the dosage (current, power or voltage) output of electrosurgical generator 20 using the calculated power factor and values of the voltage and current outputs of electrosurgical generator 20. In an AC circuit, power is determined by the formula P=|E|·|I| cos φ, where P is the power measured in watts, |E| is a voltage magnitude, |I| is a current magnitude, and φ is the phase difference between the voltage and current. Noting that since the phase information of the voltage and current by themselves is typically not required for the application, but only the cosine of the phase difference φ in calculating the power factor term (cos φ), it is possible to take advantage of Euler's Rule for calculating power. Starting with a shorthand complex notation for the voltage, $E_k[n \cdot M]$, and current, $I_k[n \cdot M]$, sensor signal outputs of equations (2a) and (2b).

$$E = \text{Real}\{E_k[n \cdot M]\} + j\text{Imaginary}\{E_k[n \cdot M]\} = a + jb; \text{ and}$$
$$|E| = \sqrt{(a^2 + b^2)}$$

$$I = \text{Real}\{I_k[n \cdot M]\} + j\text{Imaginary}\{I_k[n \cdot M]\} = c + jd; \text{ and}$$
$$|I| = \sqrt{(c^2 + d^2)}$$

Therefore, the average real power can be calculated by the dosage calculating circuit 240 as P=a·c+b·d.

Theoretically, this is all that is necessary to calculate the average real power, but if one prefers to still use the more traditional recognized form of the power equation then the following highly simplified substitution for cos(φ) may be made instead where it may be recognized from Euler's Rule that:

$$\cos(\phi) = \frac{a \cdot c + b \cdot d}{\sqrt{(a \cdot c + b \cdot d)^2 + (b \cdot c - a \cdot d)^2}}, \text{ and again} \quad (3)$$

$$P = |E| \cdot |I| \cos\varphi$$

By advantageously using the polyphase demodulation and decimation filter for a single known value of frequency, automatic control circuit 100 of the present disclosure calculates the dosage output for electrosurgical generator using fewer computational steps than a DFT. More particularly, due to the frequency of the output and the selected sampling rate for the voltage and current components of the output, there may be insufficient computational bandwidth to use a DFT to determine the power factor. However, processing circuit 210 that employs the polyphase demodulation and decimation filter determines the power factor using fewer computational steps and within the existing bandwidth.

Automatic control circuit 100 additionally calculates the dosage output of electrosurgical generator 20 and performs any necessary adjustments to the output within the existing bandwidth. In an embodiment, after automatic control circuit 100 calculates the dosage output and performs any necessary adjustments, there is additional bandwidth available before the next sample of the output is taken. Further, by using fewer computational steps to determine the power factor, minimal or no data is lost between samples.

Extra bandwidth between samples of the output is advantageously utilized to perform additional calculations, perform additional control functions, or allow the output frequency of electrosurgical generator 20 to be increased. By way of example, such additional calculations include average values of voltage and current, peak values of voltage and current, power at other frequencies and root mean square values of voltage and current. Additionally, additional control functions may include calibration of system components and adjusting system parameters for cable compensation.

Dosage calculating circuit 240 includes circuitry for determining output dosage for electrosurgical generator 20. Dosage calculating circuit 240 includes a processor and associated circuitry for determining the current, power or voltage delivered to the patient. The power factor is used to adjust the power according to the formula P=|E|·|I|cos φ or P=a·c+b·d and also adjusts the current, power or voltage delivered based on estimates of the handset cable electrical characteristics. A dosage output signal 250 is generated by dosage calculating circuit 240 and is coupled to an input of a comparison circuit 270.

Comparison circuit 270 has at least two inputs where a first input is dosage output signal 250 and a second input is a reference signal 260. Reference signal 260 is controlled by the setting of user control 160 and establishes a reference value for comparison circuit 270. In an embodiment, comparison circuit 270 includes a Digital Signal Processor and associated circuitry for determining the difference between dosage output signal 250 and reference signal 260. A feedback signal 280 is generated by comparison circuit 270 where the feedback signal 280 is representative of a RF amplitude control.

Feedback signal 280 is operatively coupled to an amplitude control for controlling the output of a drive circuit 330.

During operation of electrosurgical generator 20, drive circuit 330 produces an output that is coupled to the first winding of the transformer. A portion of the output present on the first winding of the transformer is coupled to a second winding of the transformer on leads 140 and 150. Leads 140 and 150 are electrically connected to electrodes 120 and 130 for operating an electrosurgical instrument during an electrosurgical procedure. The output present on leads 140 and 150 is sampled by voltage sensing circuit 170 and current sensing circuit 190. As discussed in detail above, the power factor is determined by processing circuit 210 and the output dosage of the electrosurgical generator 20 is determined by dosage calculating circuit 240.

As output dosage from electrosurgical generator 20 increases, the values of voltage signal 180 and current signal 200 also increase in a proportional relationship thereto. Dosage calculating circuit 240 receives output signal 220 from processing circuit 210 and determines the change in the output dosage. Accordingly, an increase in output dosage is reflected in an increase in dosage output signal 250 that is coupled to comparison circuit 270. Due to the increase in dosage output signal 250, the difference between the dosage output signal 250 and the reference signal 260 decreases resulting in a decreased feedback signal 280.

When dosage output signal 250 is substantially equal to reference signal 260, the feedback signal 280 is essentially zero. Additionally, the equality of these signals indicates that electrosurgical generator 20 is producing the desired dosage output for the selected electrosurgical procedure.

Other uses for electrosurgical generator 20 including automatic control circuit 100 are envisioned to be within the scope of this disclosure. Such applications include procedures where fine control and accuracy of delivered dosage is desirable. These applications include neurosurgical applications, ligasure sealing, thoracic and throat procedures, ocular surgery, ablation, procedures on small structures, and neonatal procedures. The determination of the power factor will allow dosage compensation so that with a known cable and handset, the dosage delivered to the patient and not just to the patient/handset/cable network can be more accurately calculated.

Further still, since automatic control circuit 100 determines the power factor of the output, this information may be coupled with known values of a handset and cable electrical characteristics (i.e., resistance, capacitance, and inductance) to determine the distance between the electrosurgical instrument and the surface of the patient. This is especially advantageous in a coagulation procedure where an electrosurgical generator is used in conjunction with an electrosurgical pencil (i.e. monopolar mode of operation) disposed above the surface of the patient. In this procedure, the electrosurgical generator typically produces a high voltage that arcs from the electrosurgical pencil to the surface of the patient, thereby coagulating affected tissue. By determining the distance between the electrosurgical pencil and the patient, automatic control circuit 10 can adjust the power output to a desired value that is sufficient to coagulate the affected tissue without producing additional power.

Using the polyphase demodulation and decimation filter has the added benefits of lower computational noise. Further, there are typically fewer computations and delays per sample for sufficiently long Discrete Fourier Transforms (DFTs). Maximally decimated filters of arbitrarily accurate passband and stopband characteristics may be used without a requirement for more complicated windowing functions. Additionally, complete frequency scalability of the filter by simply changing θk values allows variable decimation rates or filterbank processing for particular tissue effect analysis.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

The invention claimed is:

1. A system for controlling an output of an electrosurgical generator comprising:
    a drive circuit for generating an output, the output being responsive to a feedback signal and operatively coupled to at least one electrode of the electrosurgical generator;
    at least one sensing circuit operatively coupled to the at least one electrode for generating a first signal corresponding to a value of a voltage waveform present on the at least one electrode and a second signal corresponding to a value of a current waveform present on the at least one electrode;
    a processing circuit for receiving the first and second signals, wherein the processing circuit implements a heterodyne polyphase demodulation and decimation filter for determining magnitudes and a power factor based on the voltage waveform and the current waveform, wherein the heterodyne polyphase demodulation and decimation filter includes a plurality of outputs, each of which is multiplied by a complex heterodyne of the form $e^{jr\theta k}$ where r ranges from 0 to the total number of filters of the heterodyne polyphase demodulation and decimation filter minus one, θ is 2π divided by the total number of filters, and k is the ratio of a modulating frequency θ to a decimation frequency or an integer number of periods of the modulating frequency at an output sample rate, and wherein the modulating frequency is chosen in order to modulate the first signal and the second signal to a baseband frequency;
    a determining circuit in communication with the processing circuit for generating an output signal as a function of a phase difference between the voltage waveform and the current waveform and/or real power; and
    a control circuit for generating the feedback signal, the feedback signal representative of a difference between a value of the output signal and a reference value, the feedback signal operatively coupled to the drive circuit.

2. The system of claim 1, wherein the processing circuit includes at least one digital signal processor.

3. The system of claim 1, wherein the power factor is used to compensate for energy delivery at an operating site.

4. The system of claim 1, wherein the power and power factor provides feedback to the generator about tissue relating to tissue change over time, tissue impedance, tissue type or tissue cycle completion.

5. The system of claim 1, wherein the at least one sensing circuit includes a voltage sensing circuit.

6. The system of claim 1, wherein the at least one sensing circuit includes a current sensing circuit.

7. A system for controlling an output of an electrosurgical generator comprising:
    a drive circuit for generating an output, the output being responsive to a feedback signal from at least one electrode operatively coupled to the electrosurgical generator;
    at least one sensing circuit operatively coupled to the at least one electrode that generates a first signal corresponding to a value of a voltage waveform present on the at least one electrode and a second signal corresponding to a value of a current waveform present on the at least one electrode;
    a processing circuit for receiving the first and second signals, wherein the processing circuit implements a heterodyne polyphase demodulation and decimation filter for determining magnitudes and a power factor based on the voltage waveform, the current waveform, and/or real power, wherein the heterodyne polyphase demodulation and decimation filter includes a plurality of outputs, each of which is multiplied by a complex heterodyne of the form $e^{jr\theta k}$, where r ranges from 0 to the total number of filters of the heterodyne polyphase demodulation and decimation filter minus one, θ is 2π divided by the total number of filters, and k is the ratio of a modulating frequency θ to a decimation frequency or an integer number of periods of the modulating frequency at an output sample rate, and wherein the modulating frequency is chosen in order to modulate the signal to a baseband frequency, and wherein the modulating frequency is chosen to modulate the first signal and the second signal to a baseband frequency; and a determining circuit in communication with the processing circuit that generates an output signal as a function of a phase difference between the voltage waveform and the current waveform and/or the real power.

8. The system of claim 7, further comprising:

a control circuit that generates the feedback signal, the feedback signal representative of a difference between a value of the output signal and a reference value, the feedback signal operatively coupled to the drive circuit.

9. The system of claim 7, wherein the processing circuit includes at least one digital signal processor.

10. The system of claim 7, wherein the power factor is used to compensate for energy delivery at an operating site.

11. The system of claim 7, wherein the power factor provides feedback to the generator relating to tissue change over time, tissue impedance, tissue type or tissue cycle completion.

12. The system of claim 7, wherein the at least one sensing circuit includes a voltage sensing circuit.

13. The system of claim 7, wherein the at least one sensing circuit includes a current sensing circuit.

* * * * *